(12) United States Patent
Yamada et al.

(10) Patent No.: US 9,073,812 B2
(45) Date of Patent: Jul. 7, 2015

(54) ORGANIC COMPOUND

(75) Inventors: Naoki Yamada, Inagi (JP); Minako Nakasu, Tokyo (JP); Jun Kamatani, Tokyo (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 320 days.

(21) Appl. No.: 13/695,969

(22) PCT Filed: Apr. 19, 2011

(86) PCT No.: PCT/JP2011/060006
§ 371 (c)(1),
(2), (4) Date: Nov. 2, 2012

(87) PCT Pub. No.: WO2011/138907
PCT Pub. Date: Nov. 10, 2011

(65) Prior Publication Data
US 2013/0043463 A1 Feb. 21, 2013

(30) Foreign Application Priority Data
May 6, 2010 (JP) .................. 2010-106716

(51) Int. Cl.
*C07C 13/62* (2006.01)
*H01L 51/54* (2006.01)
(Continued)

(52) U.S. Cl.
CPC ............ *C07C 13/62* (2013.01); *C07C 2103/54* (2013.01); *H01L 51/0056* (2013.01);
(Continued)

(58) Field of Classification Search
CPC C07C 13/62; C07C 2103/54; H01L 51/0056; H01L 51/5012; C09K 11/06; C09K 2211/1011; C09K 2211/1007; H05B 33/10
See application file for complete search history.

(56) References Cited

U.S. PATENT DOCUMENTS

2004/0076853 A1* 4/2004 Jarikov .................. 428/690

FOREIGN PATENT DOCUMENTS

JP 2007-169581 A 7/2007
JP 2007-191603 A 8/2007
(Continued)

*Primary Examiner* — Dawn Garrett
(74) *Attorney, Agent, or Firm* — Canon USA Inc. IP Division

(57) ABSTRACT

There is provided a novel organic compound represented by following general formula [I] and that has an excellent luminescent hue and that can produce high efficiency, high-intensity, and long-life light output, and an organic light-emitting device containing the novel organic compound,

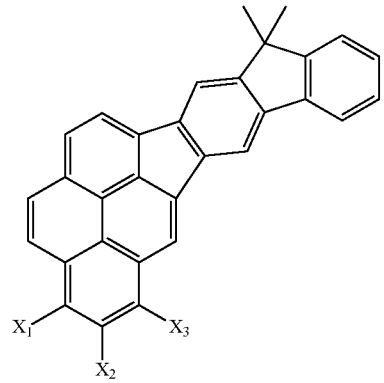

[1]

wherein $X_1$ to $X_3$ independently denote a hydrogen atom, an alkyl group, or an aryl group.

10 Claims, 1 Drawing Sheet

(51) Int. Cl.
*H01L 51/00* (2006.01)
*C09K 11/06* (2006.01)
*H05B 33/10* (2006.01)
*H01L 51/50* (2006.01)

(52) U.S. Cl.
CPC ............ *H01L51/5012* (2013.01); *C09K 11/06* (2013.01); *H05B 33/10* (2013.01); *C09K 2211/1007* (2013.01); *C09K 2211/1011* (2013.01)

(56) References Cited

FOREIGN PATENT DOCUMENTS

| | | |
|---|---|---|
| JP | 2010-111620 A | 5/2010 |
| JP | 2010-138090 A | 6/2010 |
| JP | 2011-079822 A | 4/2011 |
| WO | 2010/012330 A1 | 2/2010 |

\* cited by examiner

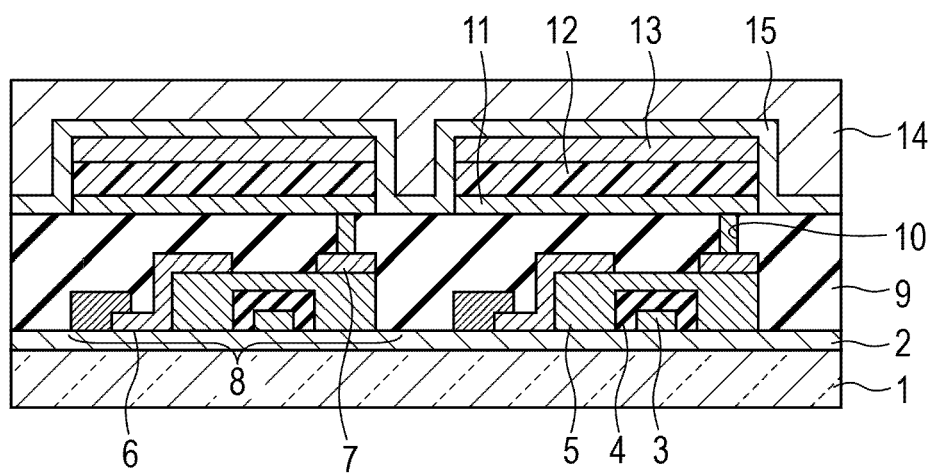

ORGANIC COMPOUND

TECHNICAL FIELD

The present invention relates to a novel organic compound and an organic light-emitting device containing the novel organic compound.

BACKGROUND ART

Organic light-emitting devices include a pair of electrodes and an organic compound layer disposed between the electrodes. Injection of carriers from the pair of electrodes excites an organic compound. Transition from the excitation state to the ground state induces light emission.

Organic light-emitting devices are also referred to as organic electroluminescent (EL) devices.

In organic light-emitting devices, it is known that an organic compound having a high quantum yield in a light-emitting layer contributes to high luminous efficiency.

PTL 1 discloses pyrene compounds, such as an exemplary compound 9, as blue-light-emitting materials. The exemplary compound 9 has a pyrene basic skeleton and a fluorenyl group and a phenyl group. The basic skeleton refers to a fused ring having a conjugated structure.

[Chem. 1]

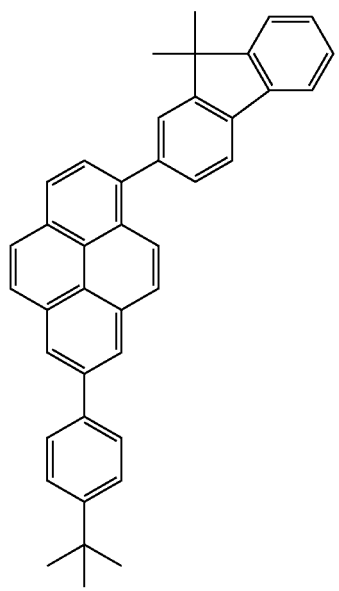

(Exemplary compound 9)

PTL 1 describes pyrene compounds. The pyrene compounds have an emission peak wavelength in a blue region and cannot emit light in a green region. Although it is known that the emission wavelength can be altered with a substituent on a basic skeleton, the substituent may impair the stability of the compound.

CITATION LIST

Patent Literature

PTL 1 Japanese Patent Laid-Open No. 2007-191603 (no foreign counterpart)

SUMMARY OF INVENTION

The present invention provides a novel organic compound the basic skeleton of which has an emission wavelength in a green region.

The present invention provides an organic compound represented by the following general formula (I):

[Chem. 2]

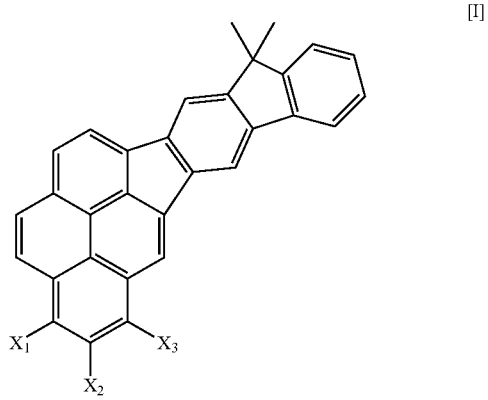

wherein $X_1$ to $X_3$ independently denote a hydrogen atom, an alkyl group, or an aryl group.

The present invention provides an organic compound the basic skeleton of which can emit light in a green region. The present invention also provides an organic light-emitting device that contains the organic compound.

BRIEF DESCRIPTION OF DRAWINGS

FIG. 1 is a schematic cross-sectional view of an organic light-emitting device and a switching device, which is connected to the organic light-emitting device.

DESCRIPTION OF EMBODIMENTS

An organic compound according to one embodiment of the present invention has the following general formula (I):

[Chem. 3]

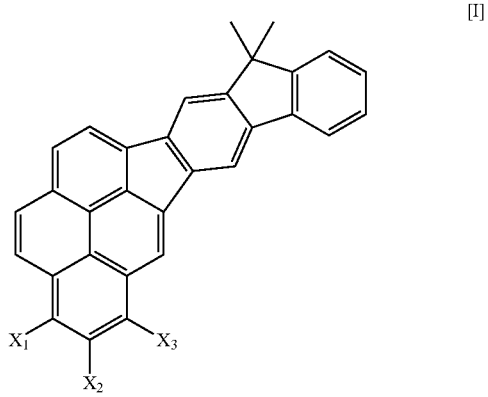

wherein $X_1$ to $X_3$ independently denote a hydrogen atom, an alkyl group, or an aryl group.

For example, the alkyl group is selected from the group consisting of a methyl group, an ethyl group, a n-propyl group, an isopropyl group, a n-butyl group, an isobutyl group, a sec-butyl group, a tert-butyl group, a cyclohexyl group, and an adamantyl group.

For example, the aryl group is selected from the group consisting of a phenyl group, a naphthyl group, a pentalenyl group, an anthryl group, a pyrenyl group, an indacenyl group, an acenaphthenyl group, a phenanthryl group, a phenalenyl group, a fluoranthenyl group, a benzofluoranthenyl group, an acephenanthryl group, an aceanthryl group, a triphenylenyl group, a chrysenyl group, a naphthacenyl group, a perylenyl group, a pentacenyl group, and a fluorenyl group.

The aryl group may have a substituent. Examples of the substituent include, but are not limited to, alkyl groups, such as a methyl group, an ethyl group, and a propyl group; aralkyl groups, such as a benzyl group and a phenethyl group; aryl groups, such as a phenyl group and a biphenyl group; heterocyclic groups, such as a thienyl group, a pyrrolyl group, and a pyridyl group; amino groups, such as a dimethylamino group, a diethylamino group, a dibenzylamino group, a diphenylamino group, a ditolylamino group, and a dianisolylamino group; alkoxy groups, such as a methoxy group, an ethoxy group, a propoxy group, and a phenoxy group; a cyano group; a nitro group; and halogen atoms, such as fluorine and chlorine.

The basic skeleton of an organic compound according to an embodiment of the present invention, that is, an organic compound having the general formula (I) in which $X_1$ to $X_3$ are hydrogen atoms has a peak wavelength of an emission spectrum in a green emission region. The term "green emission region" or "green region", as used herein, refers to a region in the range of 490 nm or more and 550 nm or less.

In an organic compound according to an embodiment of the present invention, the substitution of any of $X_1$ to $X_3$ in the general formula (I) with an aryl group can improve the oscillator strength and the quantum yield of the compound.

Any of $X_1$ to $X_3$ can be substituted with a condensed polycyclic group. Condensed polycyclic groups have high oscillator strength and can improve the quantum yield of the compound. Examples of the condensed polycyclic groups include, but are not limited to, a fluorenyl group, a naphthyl group, a pyrenyl group, a fluoranthenyl group, and a benzofluoranthenyl group.

An organic compound according to an embodiment of the present invention having the general formula (I) in which $X_1$ to $X_3$ are hydrogen atoms has high planarity. When used as a light-emitting material, therefore, this organic compound tends to cause concentration quenching. The substitution of any of $X_1$ to $X_3$ with an alkyl group or an aryl group can reduce concentration quenching.

The substitution of any of $X_1$ to $X_3$ with a condensed polycyclic group can reduce concentration quenching. This is because a bulky condensed polycyclic group can effectively reduce concentration quenching. Examples of the condensed polycyclic group include, but are not limited to, a naphthyl group, a pyrenyl group, a fluorenyl group, a fluoranthenyl group, and a benzofluoranthenyl group.

A skeleton of an organic compound according to an embodiment of the present invention involved in light emission has no rotational structure. This can reduce the conversion of the energy of the organic compound into kinetic energy, such as rotational energy or vibrational energy, thereby increasing the percentage of energy emitted as photons. In other words, this can prevent a decrease in quantum yield.

An organic compound according to an embodiment of the present invention includes two five-membered rings in its basic skeleton and strong electron-withdrawing ability.

Compounds having strong electron-withdrawing ability have a deep LUMO level. The phrase "deep LUMO level", as used herein, refers to a LUMO level far from the vacuum level.

With a constant band gap, a deep LUMO level corresponds to a deep HOMO level.

A compound having a deep HOMO level has a high oxidation potential. The oxidation of such a compound requires a large amount of energy, indicating that the compound is resistant to oxidation.

An organic compound according to an embodiment of the present invention has a deep LUMO level and is resistant to oxidation. Use of a compound that is resistant to oxidation in an organic light-emitting device can provide a stable long-life organic light-emitting device.

Organic compounds according to embodiments of the present invention are described below.

[Chem. 4]

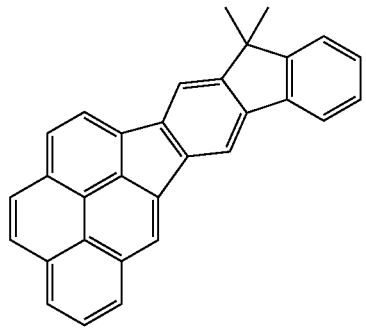

A-1

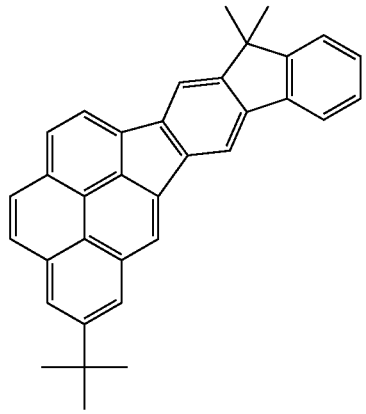

A-2

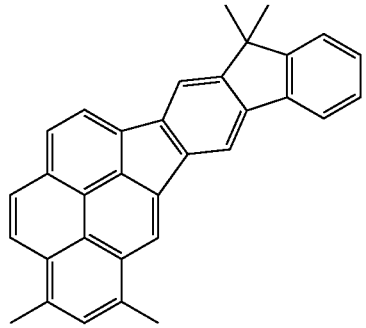

A-3

-continued
A-4
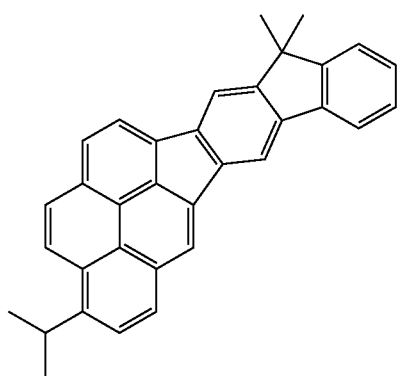
B-1
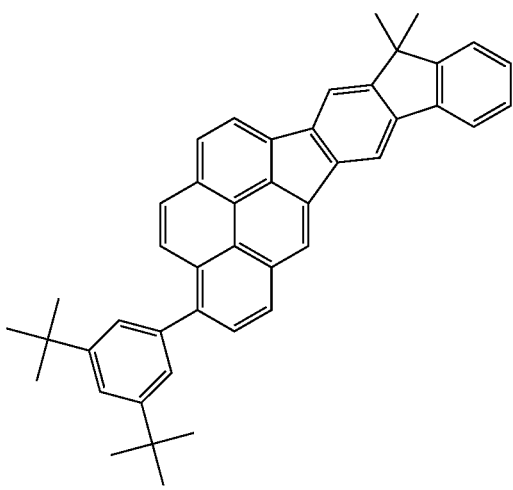
B-2
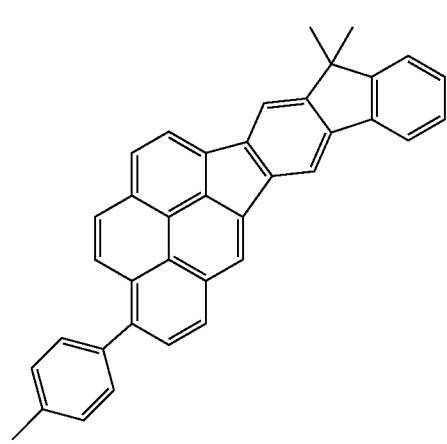
-continued
B-3
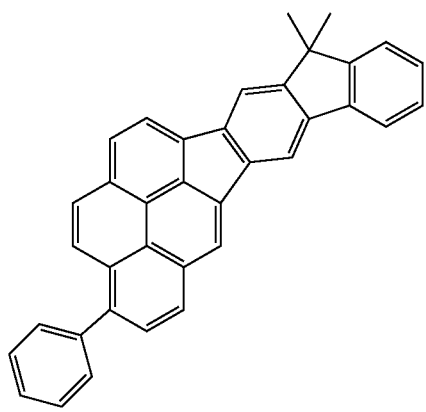
B-4
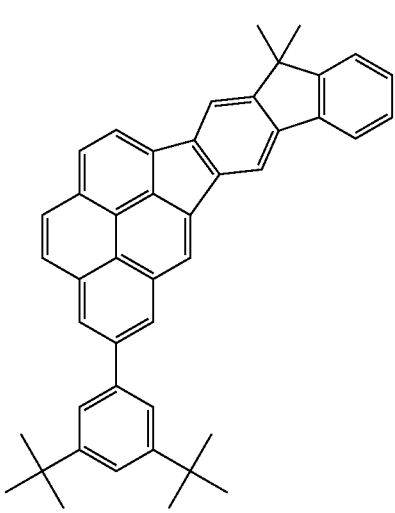
B-5
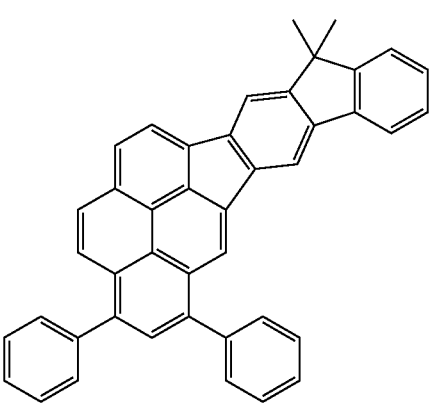

-continued
C-1
C-2
C-3
-continued
C-4
[Chem. 5]
C-6
C-7
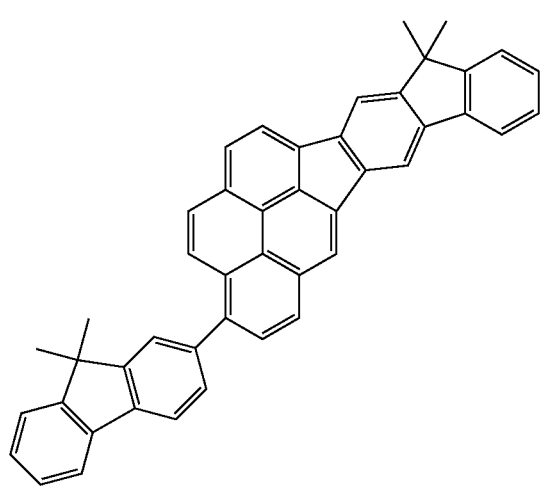
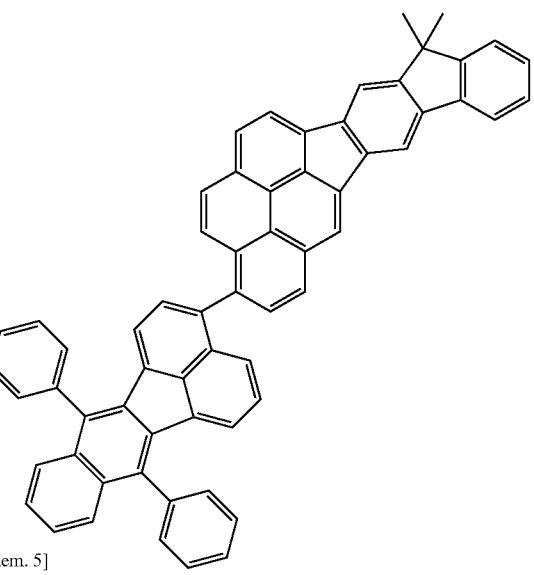

-continued

C-8

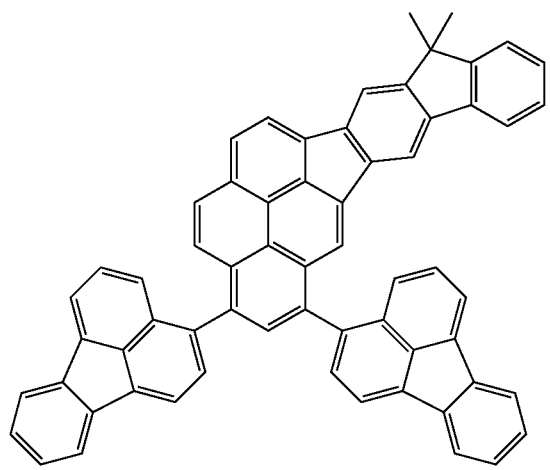

[Chem. 7]

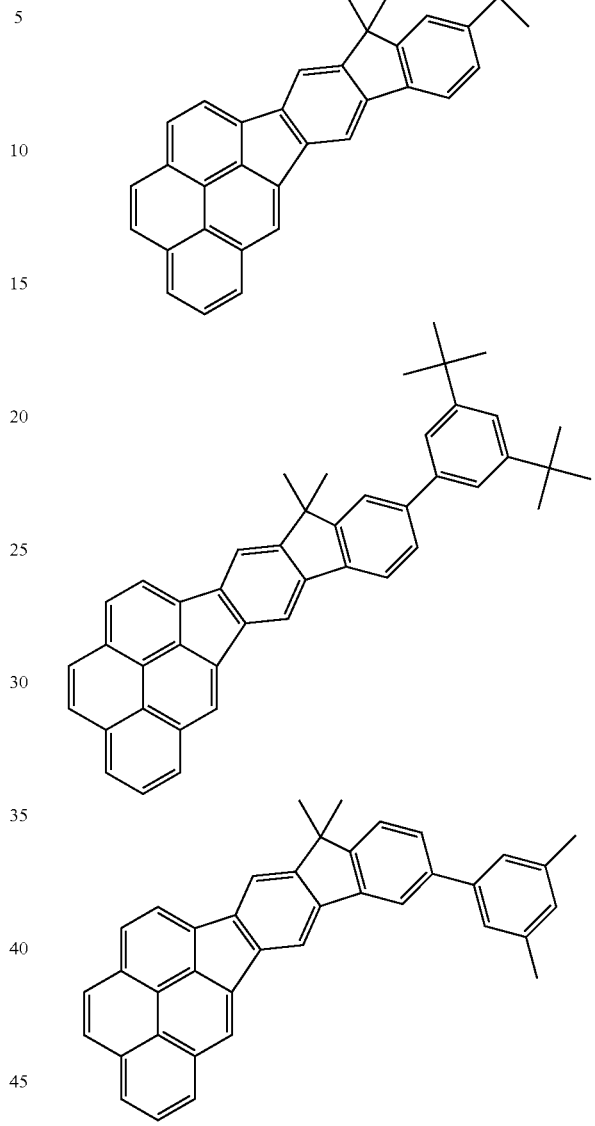

Characteristics of Exemplary Compounds

Among these exemplary compounds, compounds A-2 to A-4 have the general formula (I) in which at least one of $X_1$ to $X_3$ is an alkyl group. These compounds can greatly reduce concentration quenching.

Compounds B-1 to B-5 have the general formula (I) in which at least one of $X_1$ to $X_3$ is a phenyl group. The compounds B-1 to B-5 having substituents larger than the alkyl groups can more greatly reduce concentration quenching than the compounds A-2 to A-4. The compounds B-1 to B-5 have high oscillator strength and high quantum yields.

Compounds C-1 to C-8 have the general formula (I) in which at least one of $X_1$ to $X_3$ is a condensed polycyclic group. The compounds C-1 to C-8 having substituents larger than the alkyl groups and the phenyl groups can still more greatly reduce concentration quenching. The compounds C-1 to C-8 have higher oscillator strength and higher quantum yields than the compounds B-1 to B-5.

An organic compound according to a reference example having the following general formula (II) has substantially the same effects as the compounds having the general formula (I).

[Chem. 6]

[II]

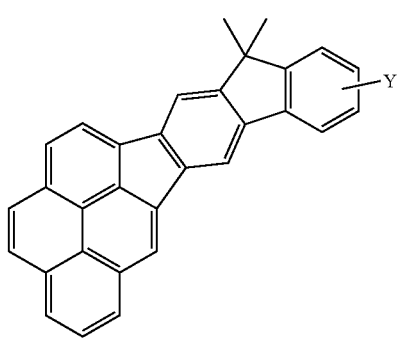

wherein Y denotes an alkyl group or an aryl group. Two or more Y's may be the same or different.

Specific examples of such a compound are described below.

An organic compound according to an embodiment of the present invention can be used in a light-emitting layer, a hole-transport layer, or an electron-transport layer of organic light-emitting devices.

Organic light-emitting devices that include a light-emitting layer containing an organic compound according to an embodiment of the present invention have high color purity, high luminous efficiency, and long life.

In a light-emitting layer containing a host material and a guest material, an organic compound according to an embodiment of the present invention can be used as the guest material.

The host material is the compound that has the highest weight percentage among the compounds composing the light-emitting layer. The guest material is a compound that has a lower weight percentage than the host material and is a principal light source.

An organic compound according to an embodiment of the present invention may be used alone in a light-emitting layer.

An organic compound according to an embodiment of the present invention may be used as a guest material.

The amount of an organic compound according to an embodiment of the present invention used as a guest material in a light-emitting layer is preferably 0.1% by weight or more and 30% by weight or less, more preferably 0.1% by weight or more and 15% by weight or less, of the total weight of the light-emitting layer. These ranges apply to the case where the light-emitting layer contains a compound other than the host material and the guest material.

A guest material in an organic compound layer may be distributed uniformly or so as to have a concentration gradient. Alternatively, a guest material may be distributed only in a certain area in an organic compound layer.

An organic compound according to an embodiment of the present invention includes two five-membered rings and is therefore resistant to oxidation. Owing to electron injection ability resulting from the electron-withdrawing ability of the five-membered ring structure, use of the organic compound as a material for an organic light-emitting device can reduce the driving voltage of the organic light-emitting device.

An organic compound according to an embodiment of the present invention may be used as an assist material.

An assist material can efficiently transfer energy from a host material to a guest material.

An organic compound according to an embodiment of the present invention has electron-withdrawing ability. Thus, the organic compound contained in a light-emitting layer as an assist material can promote electron injection into the light-emitting layer, thereby reducing the driving voltage and extending the life of the organic light-emitting device.

Description of Organic Light-Emitting Device

An organic light-emitting device according to the present embodiment includes a pair of anode and cathode and an organic compound layer disposed between the anode and the cathode. The organic compound layer contains an organic compound according to an embodiment of the present invention.

An organic compound layer of an organic light-emitting device according to the present embodiment may be composed of a plurality of layers. Examples of the plurality of layers include, but are not limited to, a hole-injection layer, a hole-transport layer, a light-emitting layer, a hole-blocking layer, an exciton-blocking layer, an electron-transport layer, and an electron-injection layer. These layers may be appropriately combined.

As a result of investigations, the present inventors found that a device that includes an organic compound according to one embodiment of the present invention as a host material or a guest material, particularly a guest material, of a light-emitting layer can efficiently output high-intensity light and have high durability.

If necessary, in addition to an organic compound according to an embodiment of the present invention, an organic light-emitting device according to the present embodiment may contain a conventionally known low-molecular-weight or high-molecular-weight hole-injection material, hole-transport material, host material, guest material, electron-injection material, or electron-transport material.

Examples of these compounds will be described below.

It is desirable that the hole-injection material or the hole-transport material be a material having high hole mobility. Examples of the low-molecular-weight and high-molecular-weight materials having hole-injection ability or hole-transport ability include, but are not limited to, triarylamine derivatives, phenylenediamine derivatives, stilbene derivatives, phthalocyanine derivatives, porphyrin derivatives, polyvinylcarbazole, polythiophene, and other electroconductive polymers.

Table 1 shows specific structural formulae of host materials. The host materials may be derivatives of the compounds having the structural formulae shown in Table 1. Other examples of the host materials include, but are not limited to, fused-ring compounds (for example, fluorene derivatives, naphthalene derivatives, anthracene derivatives, pyrene derivatives, carbazole derivatives, quinoxaline derivatives, and quinoline derivatives), organoaluminum complexes, such as tris(8-quinolinolato)aluminum, organozinc complexes, triphenylamine derivatives, and polymer derivatives, such as polyfluorene derivatives and polyphenylene derivatives.

TABLE 1

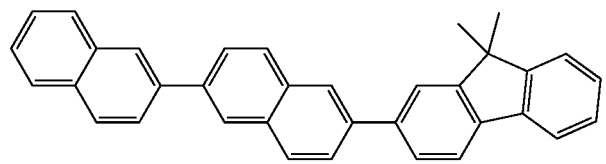 [SMILES: CC1(C)c2ccccc2-c2ccc(-c3ccc4cc(-c5ccc6ccccc6c5)ccc4c3)cc21]

1

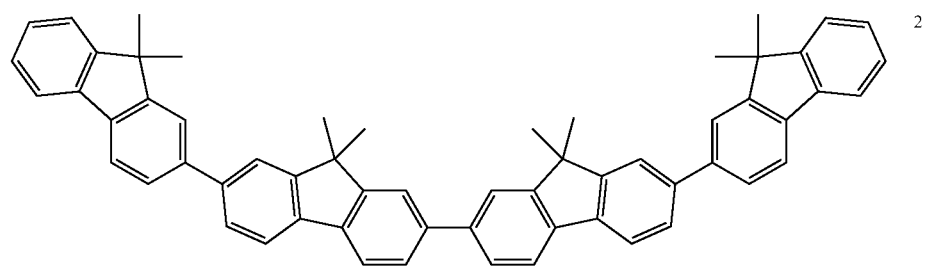

2

TABLE 1-continued
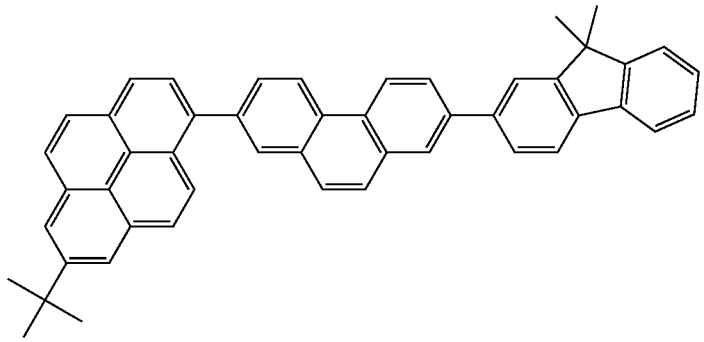 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34]
3
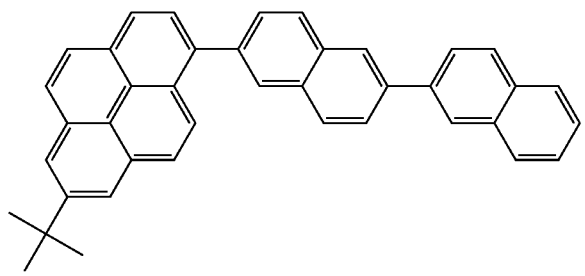 [SMILES: CC(C)(C)c1cc2ccc3ccc(-c4ccc5cc(-c6ccc7ccccc7c6)ccc5c4)c4ccc(c1)c2c34]
4
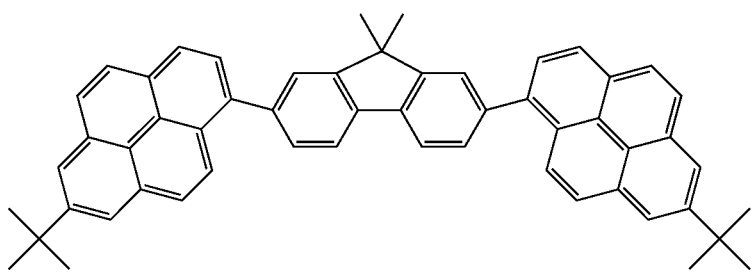 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34]
5
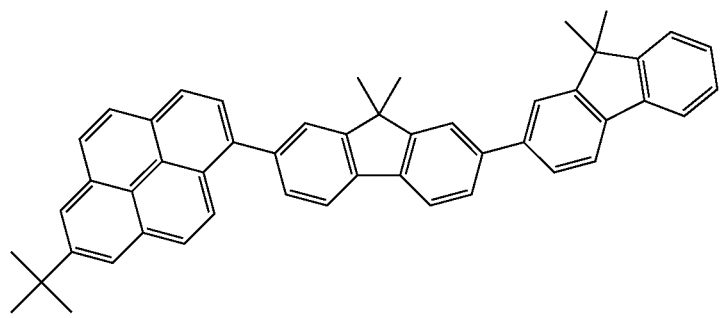 [SMILES: CC(C)(C)c1cc2ccc3ccc(-c4ccc5c(c4)C(C)(C)c4cc(-c6ccc7c(c6)C(C)(C)c6ccccc6-7)ccc4-5)c4ccc(c1)c2c34]
6
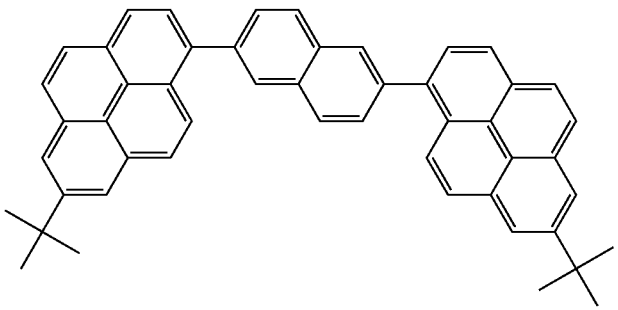 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34]
7

TABLE 1-continued
| | |
|---|---|
| 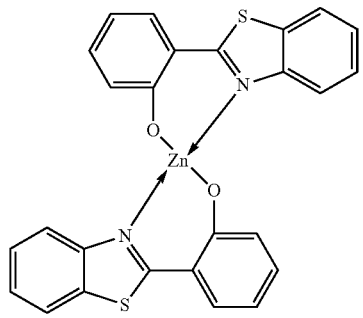 | 8 |
| 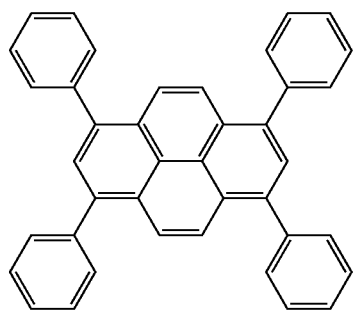 [SMILES: c1ccc(-c2cc(-c3ccccc3)c3ccc4c(-c5ccccc5)cc(-c5ccccc5)c5ccc2c3c54)cc1] | 9 |
| 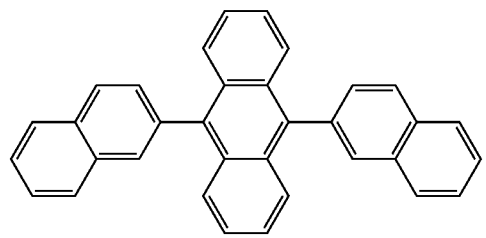 [SMILES: c1ccc2cc(-c3c4ccccc4c(-c4ccc5ccccc5c4)c4ccccc34)ccc2c1] | 10 |
| 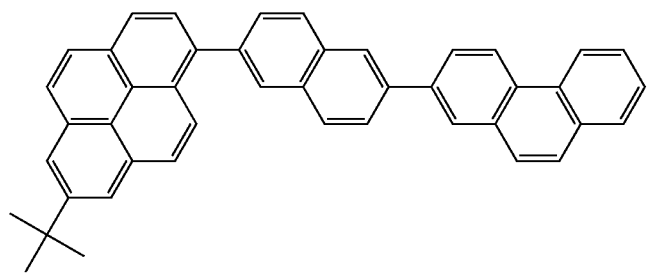 [SMILES: CC(C)(C)c1cc2ccc3ccc(-c4ccc5cc(-c6ccc7c(ccc8ccccc87)c6)ccc5c4)c4ccc(c1)c2c34] | 11 |
| 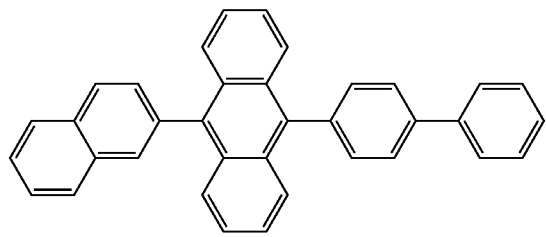 [SMILES: c1ccc(-c2ccc(-c3c4ccccc4c(-c4ccc5ccccc5c4)c4ccccc34)cc2)cc1] | 12 |

TABLE 1-continued

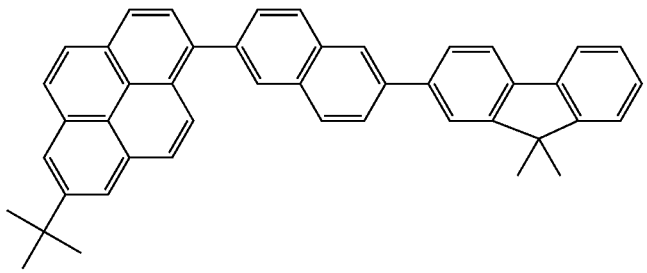 [SMILES: CC(C)(C)c1cc2ccc3ccc(-c4ccc5cc(-c6ccc7c(c6)C(C)(C)c6ccccc6-7)ccc5c4)c4ccc(c1)c2c34]

13

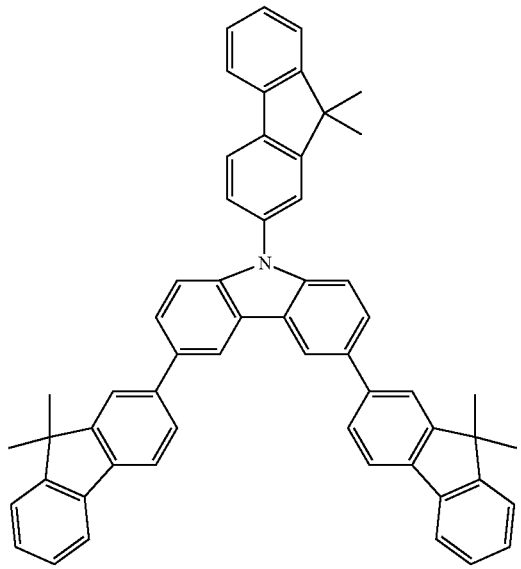

14

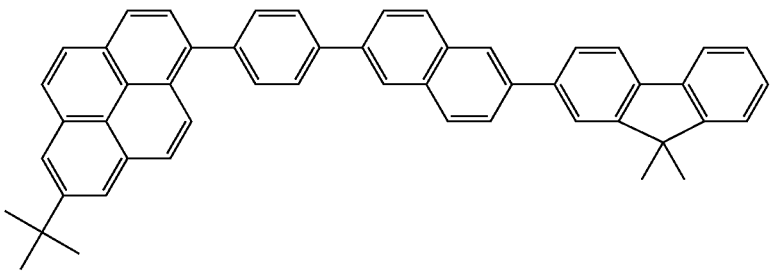 [SMILES: CC(C)(C)c1cc2ccc3ccc(-c4ccc(-c5ccc6cc(-c7ccc8c(c7)C(C)(C)c7ccccc7-8)ccc6c5)cc4)c4ccc(c1)c2c34]

15

The electron-injection material or the electron-transport material is selected in consideration of balance with hole mobility of the hole-injection material or the hole-transport material. Examples of the material having electron-injection ability or electron-transport ability include, but are not limited to, oxadiazole derivatives, oxazole derivatives, pyrazine derivatives, triazole derivatives, triazine derivatives, quinoline derivatives, quinoxaline derivatives, phenanthroline derivatives, and organoaluminum complexes.

It is desirable that the material for the anode have a work function as high as possible. Examples of the anode material include, but are not limited to, metallic elements, such as gold, platinum, silver, copper, nickel, palladium, cobalt, selenium, vanadium, and tungsten, alloys of these metallic elements, and metal oxides, such as tin oxide, zinc oxide, indium oxide, indium tin oxide (ITO), and indium zinc oxide. Examples of the anode material also include, but are not limited to, electroconductive polymers, such as polyaniline, polypyrrole, and polythiophene. These electrode materials may be used alone or in combination. The anode may have a monolayer or multilayer structure.

It is desirable that the material for the cathode have a work function as low as possible. Examples of the cathode material include, but are not limited to, alkali metals, such as lithium, alkaline-earth metals, such as calcium, and metallic elements, such as aluminum, titanium, manganese, silver, lead, and chromium. Examples of the cathode material also include, but are not limited to, alloys of these metallic elements, such as magnesium-silver, aluminum-lithium, and aluminum-magnesium. Metal oxides, such as indium tin oxide (ITO), may also be used. These electrode materials may be used alone or in combination. The cathode may have a monolayer or multilayer structure.

In an organic light-emitting device according to the present embodiment, a layer containing an organic compound according to an embodiment of the present invention and a layer containing another organic compound can be formed in the following manner. In general, the layers are formed by a vacuum evaporation method, an ionized deposition method, a sputtering method, plasma chemical vapor deposition (CVD), or a known coating method (for example, spin coating, dipping, casting, a Langmuir-Blodgett (LB) method, or an ink jet method) using a solution in an appropriate solvent. A layer formed by a vacuum evaporation method or a solution coating method experiences little crystallization and has excellent temporal stability. When the layers are formed by a coating method, an organic compound can be used in combination with an appropriate binder resin.

Examples of the binder resin include, but are not limited to, polyvinylcarbazole resins, polycarbonate resins, polyester resins, ABS resins, acrylic resins, polyimide resins, phenolic resins, epoxy resins, silicone resins, and urea resins. These binder resins may be used alone as a homopolymer or a copolymer or may be used in combination. If necessary, an additive agent, such as a known plasticizer, antioxidant, and/ or ultraviolet absorber, may be used.

Display Apparatus Including Organic Light-Emitting Device

Applications of an organic light-emitting device according to an embodiment of the present invention will be described below.

An organic light-emitting device according to an embodiment of the present invention can be used in display apparatuses and lighting apparatuses. An organic light-emitting device according to an embodiment of the present invention can also be used in exposure light sources of electrophotographic image-forming apparatuses and backlights of liquid crystal displays.

A display apparatus includes an organic light-emitting device according to an embodiment of the present invention in a display. The display includes a plurality of pixels, each of which includes an organic light-emitting device according to an embodiment of the present invention and a TFT device, which is one of switching devices. An anode or a cathode of the organic light-emitting device is connected to a drain electrode or a source electrode of the TFT device. The display apparatus can be used as an image display apparatus in personal computers (PCs). The display apparatus may be an image input apparatus that also includes an image input unit.

An image input apparatus includes an image input unit and a display. Information from an area charge-coupled device (CCD), a linear CCD, a memory card, or the like is input to the image input unit. The information is displayed on the display. An image input apparatus may be provided with an imaging optical system, constituting an image pickup apparatus, such as a digital camera. The display apparatus may have an image output function as a display for image pickup apparatuses or ink jet printers and an input function as an operation panel. With the image output function, the image input apparatus can display images based on image information from the outside. Information on image processing is input through the input function. The display apparatus may be used as a display for multifunction printers.

A display apparatus that includes an organic light-emitting device according to one embodiment of the present invention will be described below.

FIG. 1 is a schematic cross-sectional view of a display apparatus that includes an organic light-emitting device according to an embodiment of the present invention and a TFT device, which is a switching device for controlling the on-off and luminance of the organic light-emitting device. FIG. 1 illustrates two combinations of the organic light-emitting device and the TFT device. The display apparatus may further include a transistor (not shown) for controlling luminance. The display apparatus drives the switching devices in accordance with information to turn on or off the organic light-emitting device, thereby transmitting information. The structure of the display apparatus will be described in detail below.

The display apparatus illustrated in FIG. 1 includes a substrate 1, for example, made of glass, a moisture-proof film 2 for protecting the TFT devices or an organic compound layer, metallic gate electrodes 3, a gate-insulating film 4, and a semiconductor layer 5.

Each of TFT devices 8 includes a semiconductor layer 5, a drain electrode 6, and a source electrode 7. The TFT devices 8 are covered with an insulating film 9. Each of anodes 11 of the organic light-emitting devices is connected to the corresponding source electrode 7 through a contact hole 10. The display apparatus may have any structure provided that the anode or the cathode of each of the organic light-emitting devices is connected to the source electrode or the drain electrode of the corresponding TFT device.

A multilayer organic compound layer 12 is illustrated as a single layer in FIG. 1. Cathodes 13 are covered with a first protective layer 14 and a second protective layer 15 for preventing degradation of the organic light-emitting devices.

EXAMPLES

Example 1

Synthesis of Exemplary Compound A-1

An exemplary compound A-1 was synthesized in accordance with the following scheme.

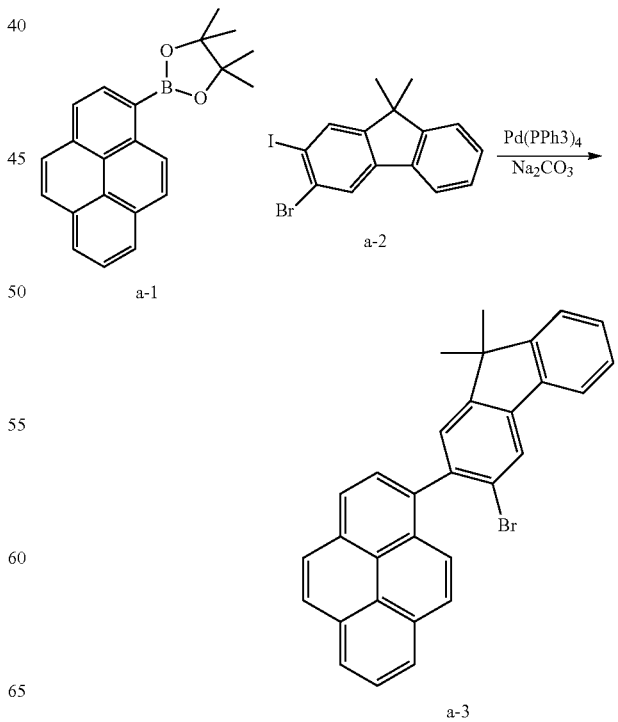

-continued

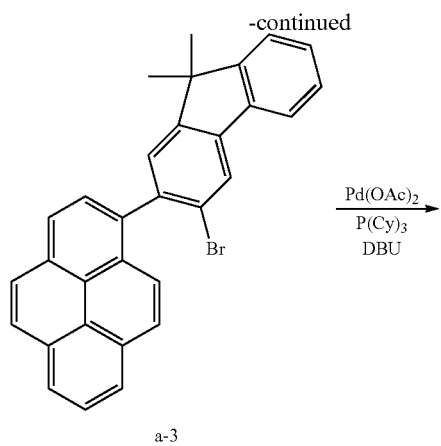

a-3

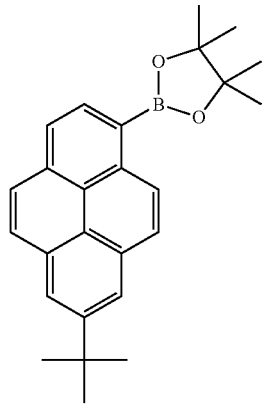

A-1 a) Synthesis of Compound a-3

0.984 g (3.00 mmol) of a compound a-1, 1.0 g (2.52 mmol) of a compound a-2, 20 ml of toluene, and 10 ml of ethanol were stirred in a 50-ml three-neck flask in a nitrogen atmosphere at room temperature. An aqueous solution of 5 g of cesium carbonate in 20 ml of water was added dropwise, and then 144 mg of tetrakis(triphenylphosphine)palladium(0) was added. The solution was heated to 77° C. and was stirred for five hours. After the reaction, an organic layer was extracted with chloroform, was dried over anhydrous sodium sulfate, and was purified through a silica gel column (with a developing solvent of toluene and heptane), yielding 1.10 g of a compound a-3 (yellow crystal) (yield 77.6%).

a) Synthesis of Exemplary Compound A-1

A 50-ml three-neck flask was charged with 1.0 g (2.12 mmol) of the compound a-3, 25 mg of palladium acetate, 1.28 ml of diazabicycloundecene (DBU), 59 mg (0.212 mmol) of tricyclohexylphosphine, and 30 ml of DMF. After agitation in a nitrogen atmosphere at room temperature, the solution was heated to 150° C. and was stirred for five hours. After the reaction, an organic layer was extracted with chloroform, was dried over anhydrous sodium sulfate, and was purified through a silica gel column (with a developing solvent of toluene and heptane), yielding 590 mg of an exemplary compound A-1 (yellow crystal) (yield 70.8%).

The mass spectrometry showed a peak at m/z of 392, which was assigned to $M^+$ of the exemplary compound A-1.

$^1$H NMR measurement demonstrated the structure of the exemplary compound A-1.

$^1$H NMR (CDCl$_3$, 400 MHz) σ (ppm): 8.64 (s, 1H), 8.46 (s, 1H), 8.43 (d, 1H), 8.39 (d, 1H), 8.27-8.23 (m, 2H), 8.13 (d, 1H), 8.08-8.04 (m, 3H), 7.89 (d, 1H), 7.50 (s, 1H), 7.44-7.38 (m, 2H), 1.65 (s, 6H)

The fluorescence spectrum of a toluene solution of the exemplary compound A-1 at a concentration of 1×10$^{-5}$ mol/l was measured with F-4500 manufactured by Hitachi, Ltd. at an excitation wavelength of 370 nm. A first emission peak wavelength in the fluorescence spectrum was 513 nm.

Example 2

An exemplary compound A-2 was synthesized in the same manner as in Example 1 except that the compound a-1 was replaced with a compound described below. The reaction yields were 70.5% at the first stage and 65.4% at the second stage.

The mass spectrometry showed a peak at m/z of 448, which was assigned to $M^+$ of the exemplary compound A-2.

[Chem. 9]

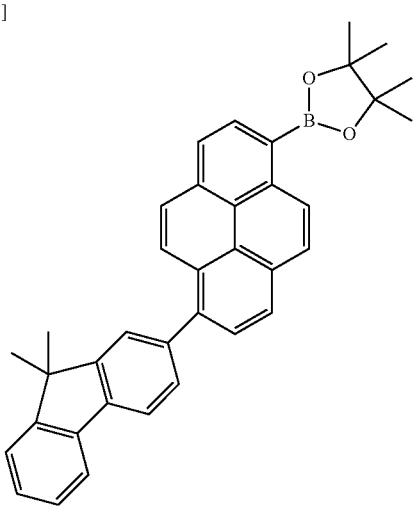

Example 3

An exemplary compound C-1 was synthesized in the same manner as in Example 1 except that the compound a-1 was replaced with a compound described below. The reaction yields were 73.2% at the first stage and 60.4% at the second stage.

The mass spectrometry showed a peak at m/z of 584, which was assigned to $M^+$ of the exemplary compound C-1.

[Chem. 10]

Synthesis Example

Exemplary compounds A-3, A-4, C-4, and C-6 can be synthesized in the same manner as in Example 1 except that the compound a-1 is replaced with pinacolboranes shown in Table 2.

TABLE 2
| Exemplary compound No. | Pinacolboranes |
|---|---|
| A-3 | 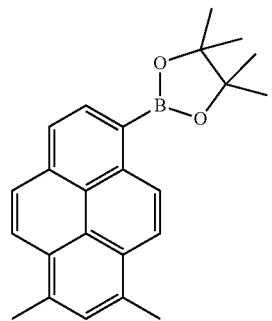 [SMILES: Cc1cc(C)c2ccc3c(B4OC(C)(C)C(C)(C)O4)ccc4ccc1c2c43] |
| A-4 | 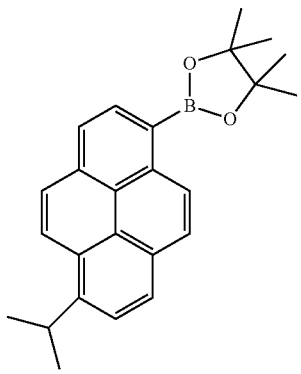 [SMILES: CC(C)c1ccc2ccc3c(B4OC(C)(C)C(C)(C)O4)ccc4ccc1c2c43] |
| C-4 | 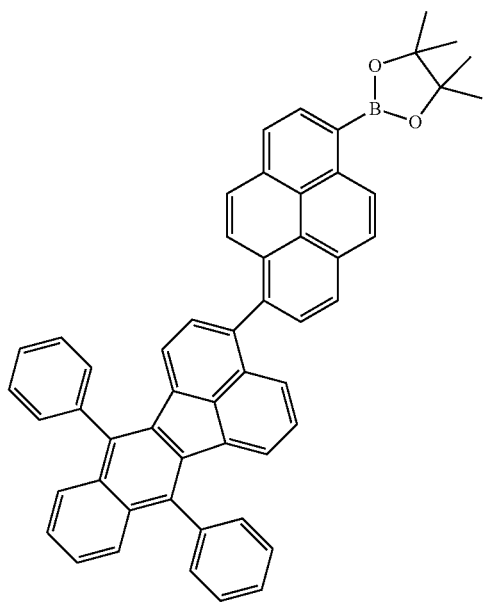 [SMILES: CC1(C)OB(c2ccc3ccc4c(-c5ccc6c7c(cccc57)-c5c-6c(-c6ccccc6)c6ccccc6c5-c5ccccc5)ccc5ccc2c3c54)OC1(C)C] |

TABLE 2-continued

| Exemplary compound No. | Pinacolboranes |
|---|---|
| C-6 | 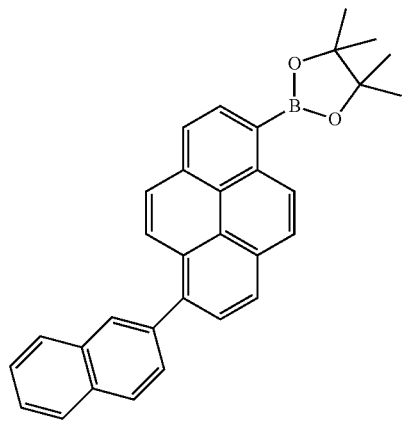 [SMILES: CC1(C)OB(c2ccc3ccc4c(-c5ccc6ccccc6c5)ccc5ccc2c3c54)OC1(C)C] |

Example 4

Fabrication of Device

An indium tin oxide (ITO) film having a thickness of 120 nm was formed as an anode on a glass substrate by sputtering. This substrate was used as a transparent electroconductive supporting substrate. The transparent electroconductive supporting substrate was subjected to ultrasonic cleaning in acetone and then isopropyl alcohol (IPA), was washed in boiled IPA, and was dried. The transparent electroconductive supporting substrate was then subjected to UV/ozone cleaning.

The following organic layer and electrode layers were formed on the transparent electroconductive supporting substrate in a vacuum chamber at $1\times10^{-5}$ Pa by vacuum evaporation using resistance heating, thus fabricating a device.

Hole-transport layer (20 nm): Compound b-1

Light-emitting layer (40 nm): Exemplary compound A-1 (weight concentration 2%):compound b-2 (weight concentration 98%)

Electron-transport layer (20 nm): Compound b-3

Metal electrode layer 1 (0.5 nm): LiF

Metal electrode layer 2 (150 nm): Al

[Chem. 11]

b-1

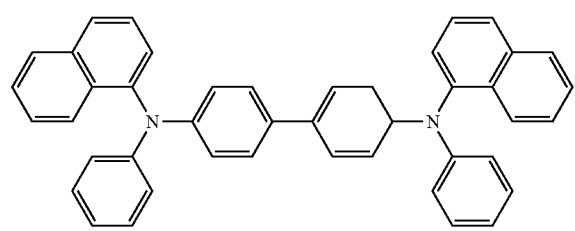

b-2

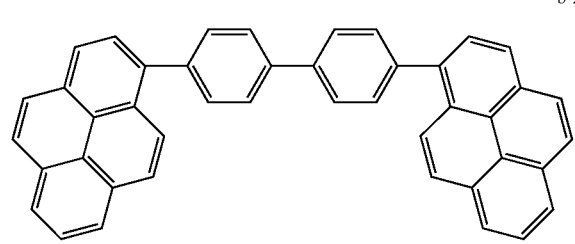

-continued b-3

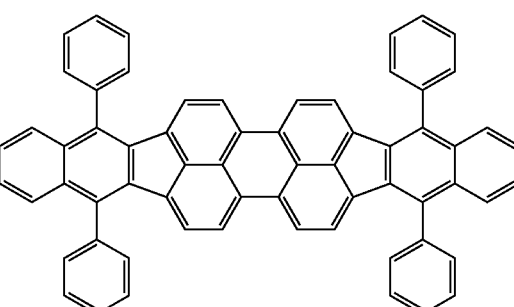

An organic light-emitting device according to the present example emitted excellent green light at an applied voltage of 5.0 V. The light had a luminance of 1113 cd/m² and a CIE chromaticity of (0.37, 0.56).

When a voltage was continuously applied to the organic light-emitting device in a nitrogen atmosphere at an electric current density of 100 mA/cm² for 100 hours, the luminance degradation rate after 100 hours was as small as 20% or less.

Example 5

A device was fabricated and evaluated in the same manner as in Example 4 except that the composition of the light-emitting layer was altered as follows:

Light-emitting layer (40 nm): Exemplary compound A-1 (weight concentration 2%):compound b-4 (weight concentration 2%):compound b-2 (weight concentration 96%)

[Chem. 12]

b-4

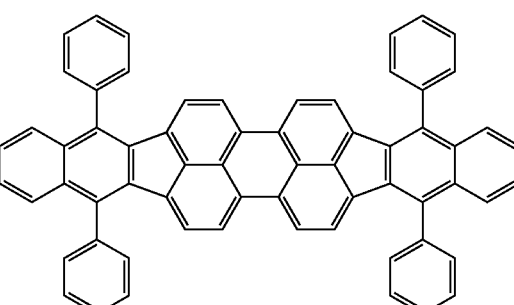

An organic light-emitting device according to the present example emitted excellent red light at an applied voltage of 5.0 V. The light had a luminance of 50 cd/m² and a CIE chromaticity of (0.32, 0.67).

When a voltage was continuously applied to the organic light-emitting device in a nitrogen atmosphere at an electric current density of 100 mA/cm² for 100 hours, the luminance degradation rate after 100 hours was as small as 20% or less.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-106716, filed May 6, 2010, which is hereby incorporated by reference herein in its entirety.

REFERENCE SIGNS LIST

8 TFT device
11 Anode
12 Organic compound layer
13 Cathode

The invention claimed is:

1. An organic compound represented by the following general formula [I]:

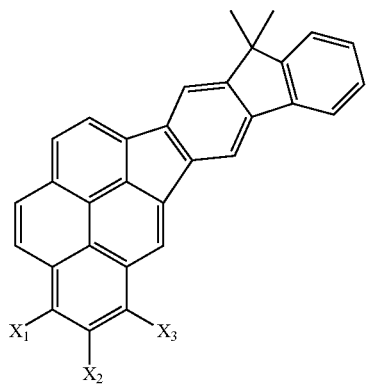

wherein $X_1$ to $X_3$ independently denote a hydrogen atom, an alkyl group, or an aryl group, wherein the aryl group is selected from the group consisting of a phenyl group, a naphthyl group, a fluorenyl group, a pyrenyl group, a fluoranthenyl group, and a benzofluoranthenyl group, the alkyl group is selected from the group consisting of a methyl group, an ethyl group, a n-propyl group, an isopropyl group, a n-butyl group, an isobutyl group, a sec-butyl group, a tert-butyl group, a cyclohexyl group, and an adamantyl group, and the aryl group may further have a substituent selected from the group consisting of a methyl group, an ethyl group, a n-propyl group, an isopropyl group, a n-butyl group, an isobutyl group, a sec-butyl group, and a tert-butyl group.

2. The organic compound according to claim 1, wherein any of $X_1$ to $X_3$ is the aryl group.

3. The organic compound according to claim 1, wherein any of $X_1$ to $X_3$ is the alkyl group.

4. An organic light-emitting device comprising:
a pair of electrodes; and
an organic compound layer disposed between the pair of electrodes,
wherein the organic compound layer contains an organic compound according to claim 1.

5. The organic light-emitting device according to claim 4, wherein the organic compound layer is a light-emitting layer.

6. A display apparatus comprising a plurality of pixels, wherein each of the pixels includes an organic light-emitting device according to claim 4 and a switching device connected to the organic light-emitting device.

7. An image input apparatus comprising:
a display configured to display information; and
an input unit to which the information is to be input,
wherein the display includes a plurality of pixels, and each of the pixels includes an organic light-emitting device according to claim 4 and a switching device connected to the organic light-emitting device.

8. A lighting apparatus comprising the organic light-emitting device according to claim 4.

9. An electrophotographic image-forming apparatus comprising an exposure light source;
wherein the exposure light source comprises the organic light-emitting device according to claim 4.

10. An exposure light source of electrophotographic image-forming apparatus comprising the organic light-emitting device according to claim 4.

* * * * *